United States Patent [19]

Bailey

[11] Patent Number: 4,521,975
[45] Date of Patent: Jun. 11, 1985

[54] LYOPHILIZING AND FORMING BIOLOGICALS HAVING A PREDETERMINED UNIT DOSAGE

[75] Inventor: Donald L. Bailey, Thornton, Colo.

[73] Assignee: Marquest Medical Products, Inc., Englewood, Colo.

[21] Appl. No.: 403,309

[22] Filed: Jul. 30, 1982

Related U.S. Application Data

[62] Division of Ser. No. 260,179, May 4, 1981, abandoned.

[51] Int. Cl.³ .............................................. F26B 5/06
[52] U.S. Cl. ........................................... 34/5; 536/21
[58] Field of Search ................................ 536/21; 34/5

[56] References Cited

U.S. PATENT DOCUMENTS

| | | | |
|---|---|---|---|
| 3,199,217 | 8/1965 | Oldenkamp et al. | 34/5 |
| 4,001,944 | 1/1977 | Williams | 34/5 |
| 4,305,502 | 12/1981 | Gregory et al. | 34/5 |

Primary Examiner—John J. Camby
Attorney, Agent, or Firm—Sheridan, Ross & McIntosh

[57] ABSTRACT

A pledget of biological material of predetermined unit dosage is formed by a lyophilizing process. The lyophilizing process involves establishing a specific batch volume of sterile water, dissolving a preestablished amount of biological material in the batch volume of water, filling at least one container with a portion of the solution of water and dissolved material, and lyophilizing the solution in the container into the pledget. The amount of biological material to be dissolved in the water is established in relation to the volume and number of containers, the desired predetermined unit dosage of each pledget, and the desired number of pledgets to be formed at a time.

7 Claims, 8 Drawing Figures

LYOPHILIZING AND FORMING BIOLOGICALS HAVING A PREDETERMINED UNIT DOSAGE

CROSS REFERENCE TO RELATED APPLICATIONS

The present application is a divisional application of U.S. patent application Ser. No. 260,179, filed May 4, 1981, now abandoned, for METHOD AND APPARATUS FOR FREEZE-DRYING BIOLOGICALS HAVING A PREDETERMINED UNIT DOSAGE, assigned to the assignee hereof.

BACKGROUND OF THE INVENTION

1. Field of Invention

The present invention relates to a method and apparatus for freeze drying or lyophilizing biologicals. More particularly, the present invention relates to freeze drying biologicals of the type that are used as anticoagulants in blood-gas analysis.

2. Description of the Prior Art

The method of first freezing and then drying biologicals by sublimation of ice in a vacuum has been known for many years. Freeze drying, or lyophilization, is similar to ordinary vacuum distillation, with the exception that the material to be dried must be frozen below its eutectic point prior to drying under very low absolute pressure during controlled heat input.

A great deal of freeze drying is done in laboratory research. Commercial applications of the process are widely accepted throughout the health profession because of the greatly enhanced storage capacity of freeze dried biologicals. There are basically three main methods for preparing materials for lyophilization in a freeze dryer.

The first method of preparation involves simply placing the material into a tray and lyophilizing the entire product in bulk. In a second method, the same, or very similar, trays can be utilized to support flasks or serum bottles during the lyophilizing process. This third method applies to very small quantities for specialized research. In the third method, ampules are connected to manifolds available on many freeze dryers. The ampules contain the materials without any tray whatsoever.

Trays are therefore well known for use with chamber freeze dryers. Variations of the trays include removable bottoms to enhance heat transferred during the dry heat portion of the lyophilization process. Wire mesh bottomed trays can be used for solid, undissolved materials having sufficient bulk to span the mesh, or can support bottles of sufficient size. Filter sealed trays are also available that include a top having a filter media incorporated therein for trapping "fly-away" products.

However, none of the trays of the prior art are well suited for producing a final product in the form of individual unit dosages. In fact, the concept of storing a preset dosage of a given biological in a ready-to-use condition has only been recently developed. For example, the reader is referred to U.S. Pat. No. 4,206,768 to Bailey, that patent having common ownership with the present invention. Thus, none of the prior art trays are very well suited for producing a pledget, or single unit dosage, of freeze dried biological material having a preset unit value, units being defined by the *United States Pharmacopoeia* (U.S.P.).

Heparin is an anticoagulant derived from porcine intestinal mucosa or beef lung. This anticoagulant is extremely valuable in obtaining human blood samples and preventing coagulation of the blood prior to blood-gas analysis or other blood tests. The principal method for utilizing heparin in aspirating a blood sample has been by use of a syringe to draw a set volume of heparin solution from a vial of heparin. This usually involves drawing out more of the heparin than is needed and then expelling the excess. The blood sample is then taken in the normal manner. If the heparin were already in the syringe, ready for use and of a specific concentration, then the procedure would be extremely quick, without the need to measure out any solution.

U.S. Pat. No. 4,257,426, issued 3-24-81, to Bailey, also of common ownership with this application, shows a heparin flake, of preset unit dosage, already placed within the barrel of a syringe. The flake is formed by allowing a solution of heparin to evaporate, and does not therefore give the extended storage life associated with freeze drying.

OBJECTS AND SUMMARY OF THE INVENTION

The principal object of the present invention is to provide a method and apparatus for lyophilization biologicals in individual dosages of predetermined U.S.P. unit value.

It is a further object of the present invention to provide improved performance of a lyophilization process for biologicals in order to form a pledged of predetermined dosage more quickly, more efficiently and more economically.

It is a further object of the present invention to increase the storage life of biologicals.

It is a related object of the present invention to provide a ready-to-use apparatus for treating aspirated blood samples.

It is a still further related object of the present invention to provide a method for using a freeze dried pledget in a syringe to preserve a blood sample that is simple and reduces the chance for error.

In accordance with the objects of the present invention, a laminated, flat, planar tray having an upper plate laminate with rows and columns of wells formed in an upper surface thereof is provided. The wells are adapted to hold a solution of biological material of a predetermined concentration. A plurality of trays may be supported on superimposed thermally controlled shelves of a freeze dryer. The wells have a volume computed so as to be compatible with a predetermined concentration of biological solution, such that, when the wells are filled with solution and after completion of a freeze drying or lyophilization process, a pledget of dried material remains in the wells of the tray having a predetermined U.S.P. unit value dosage.

The upper plate laminate of the tray has formed or joined thereto a lower laminate in the form of a sheet of conducting material adapted to help establish a temperature gradient across the height of the tray, to assist in the freezing of the tray contents, as the tray sits on the cooling or heating shelves of the freeze dryer. The top surface of the tray, in which the wells are formed, is covered by an insulator during the freezing portion of the lyophilization process to thereby keep the upper portion of the wells insulated from the upper adjacent cooling shelf of the freeze dryer, again helping to maintain the temperature gradient.

The pledget product of the freeze drying process is particularly useful when an anticoagulant is freeze dried, for instance, heparin. The pledget can be stored for long periods of time within a sterile syringe. When it is necessary to aspirate a blood sample, a needle is attached to the syringe and a blood sample withdrawn, automatically mixing with and being treated by the anticoagulant heparin, without the need for measuring out a set amount of heparin solution.

DESCRIPTION OF THE PREFERRED EMBODIMENT

Figure 1:
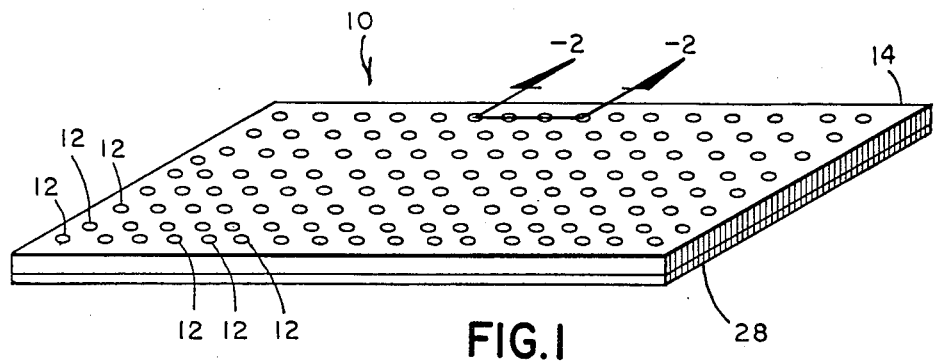
FIG. 1 is a perspective view of a tray of the present invention adapted for use in a lyophilization process.
Figure 2:
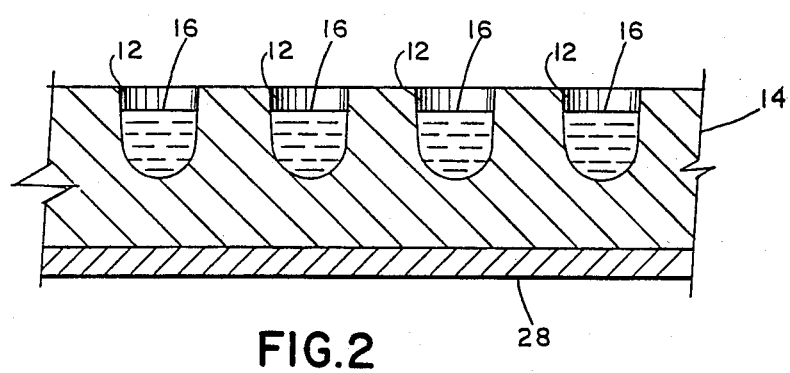
FIG. 2 is a fragmentary enlarged section view taken in a plane of line 2—2 of FIG. 1.

A laminated tray 10 having rows and columns of wells 12 formed in a top surface thereof used in a lyophilization process for primarily biological drugs and other pharmaceuticals is seen in FIGS. 1 and 2. The wells or molds 12 are drilled or formed in an upper plate laminate 14 of the tray, and the wells are of a predetermined volume. The wells 12 are adapted to be filled with a solution 16 (FIGS. 2 and 4) of predetermined concentration of the biological to be lyophilized of freeze dried. The wells 12 will be seen to correspond to a single unit dosage of whatever biological is lyophilized. As relates to this description, the solution 16 is a heparin solution.

Figure 6:
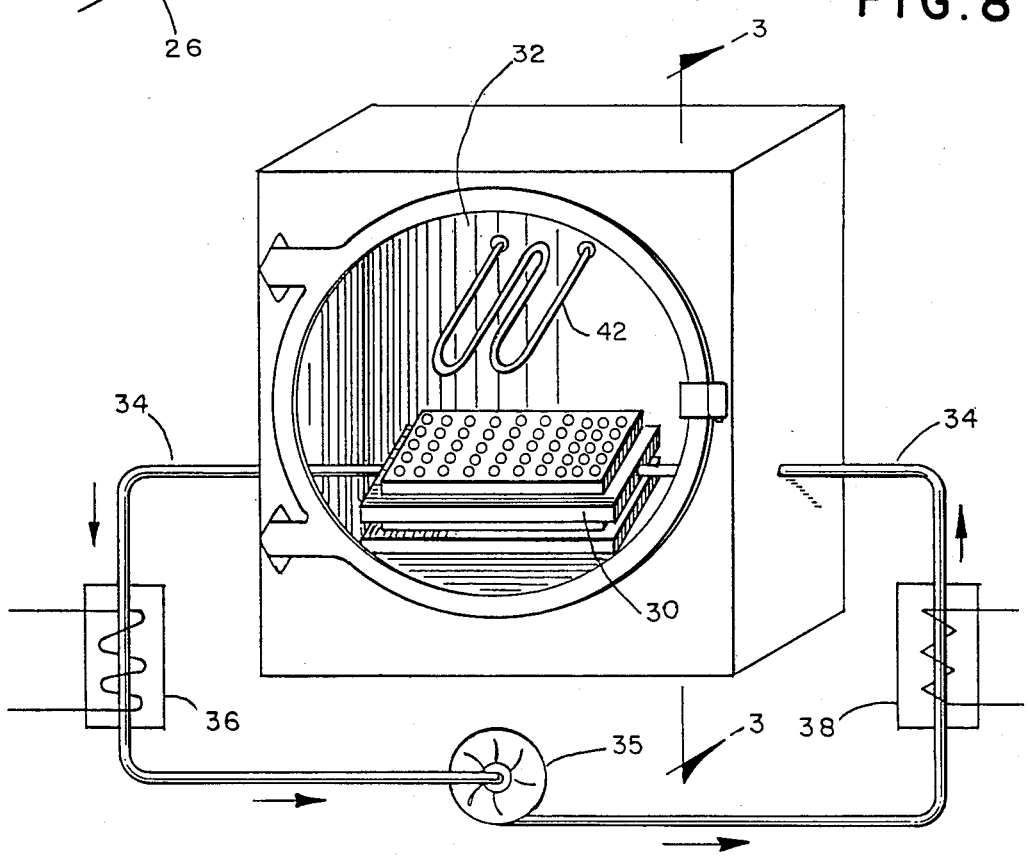
FIG. 6 is a diagrammatic view of a freeze dryer and associated system utilizing the tray shown in FIG. 1.

The tray 10 of wells 12 containing the solution 16 is placed in a commercially available freeze dryer 18 (FIGS. 6 and 7), where the solution 16 undergoes a lyophilization process, to be described in more detail hereinafter. Generally, the water content of the solution 16, in the form of an ice matrix, which matrix is formed by freezing the solution, is selectively removed by sublimation, drying and heating under vacuum conditions, during the lyophilization process. The product of the process is a dry, solid heparin pledget or flake 20, which pledget has no significant water content and is therefore capable of being stored for extended periods of time.

The tray 10 includes the upper plate laminate 14 which is made of a hard plastic like Delrin, made by the DuPont NeMours Corporation, and a lower laminate 28 of conducting material, like aluminum, bonded thereto. The tray is of rectangular solid configuration of relatively narrow thickness. The wells 12 are of dome-like shape and are formed in the plastic laminate plate 14 in rows and columns over the face of the tray 10.

Figure 3:
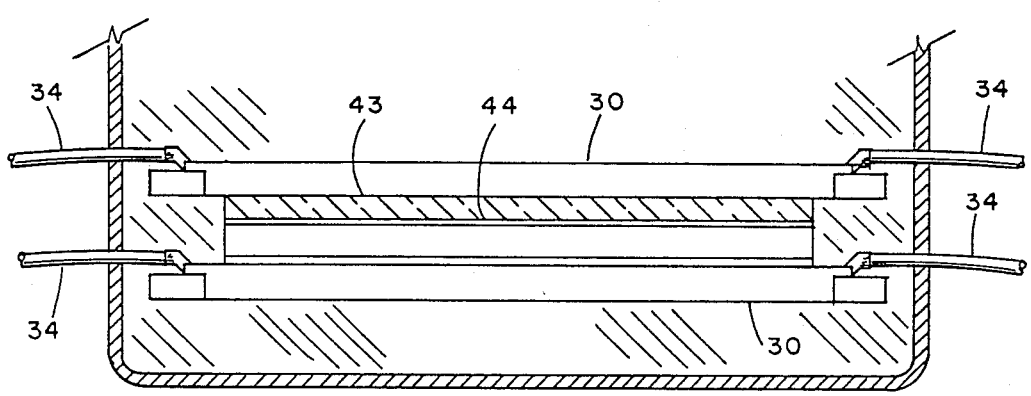
FIG. 3 is a fragmentary schematic sectional view of a freeze dryer, a pair of superimposed heating shelves, intermediate insulation and the tray shown in FIG. 1 shown in full.

The tray 10 is particularly suited to conducting the cold temeratures, around minus forty degrees Centigrade, encountered in the freeze dryer 18, necessary to the lyophilization process. A lower laminate of conducting material 28 (FIGS. 1 and 2), preferably made of aluminum sheet, is formed or bonded to the entire underneath surface of the upper plate 14. The molds or wells 12 of the tray 10 are spaced in rows and columns over the entire top surface of the upper plate 14. The holes or wells 12 in the preferred embodiment number one thousand one hundred thirty-six per tray. The trays are sized to that several trays are placed on a single thermally controlled shelf 30, a plurality of which shelves are mounted in a superimposed relationship within the freeze dryer 18 (FIG. 3). It can therefore be seen that several thousand individual heparin pledgets 20 are made in a single lyophilization cycle.

The wells 12 of the tray 10 are formed into the upper plate 14 in such a manner as to have a set or predetermined volume. The volume corresponds to a set number of single dosage units of heparin, units being defined as in the *United States Pharmacopeia* (U.S.P.), when the solution 16 to fill the predetermined volume is at a set concentration of heparin dissolved in sterile water. Usually one hundred or two hundred units are contained in a single dosage pledget 20.

The wells 12 are configured in an inverted dome shape (FIG. 2). For a unit dosage of one hundred units, the wells 12 have downwardly and inwardly sloping sides, with a bore of 0.165 inches. The wells descend 0.093 inches into the plate 14 and terminate in a dome shape, and therefore have a volume of 73.3 microliters for a one hundred unit pledget 20. These wells 12 are small enough in diameter, or bore, to be filled, when immersed in the solution 16 (FIG. 4) by capillary action. The dome shape and inward sloping sides facilitate removal of the pledgets after freeze drying.

The conducting material 28 assists in initial heat transfer to the tray 10 to thereby freeze the solution 16 contained in the wells 12, and then later applying the heat of sublimation to the solution. It has been found that, during the freezing step of lyophilization, it is desirable to freeze the solution 16 from the bottom to the top of the well 12. A temperature gradient wherein the solution 16 at the bottom of the well is cooler than the solution at the top of the well 12 is maintained both by the conducting material 28, bonded to the lower surface of the upper plate 14, and by insulating the top of the upper plate 14 from the next upper shelf 30 (FIG. 3). An insulator 43, such as Styrofoam, with an intermediate plexiglass sheet 44, is placed over the plate 14. The insulator 43 is preferably wrapped in aluminum foil to augment its insulation properties. The insulator 43 maintains the temperature gradient desired, slightly warmer at the top of the well 12 than at the bottom, while the plexiglass sheet 44 prevents Styrofoam or any other contaminant from entering the solution 16 in the wells 12.

An appropriate freeze dryer 18 is required, such as the model 25 S.R.C. built by The Virtis Company, Inc., of Gardiner, N.Y. The freeze dryer 18 (FIGS. 6 and 7) typically includes a drying chamber 32, which chamber contains the trays 10 and product solution 16 to be lyophilized. The trays are supported on the several superimposed thermally controlled shelves 30 (FIG. 3). The shelves 30 have passageways (not shown) which are connected to conduits 34 through which a liquid cooling and heating medium flows (FIG. 3). The liquid or fluid medium is pumped by a centrifugal pump 35 (FIG. 6) through the conduit 34, the shelves 30, a fluid cooler 36 and a fluid heater 38. Depending on the particular step in the lyophilization process, the cooler 36 or the heater 38 would be activated.

Figure 7:
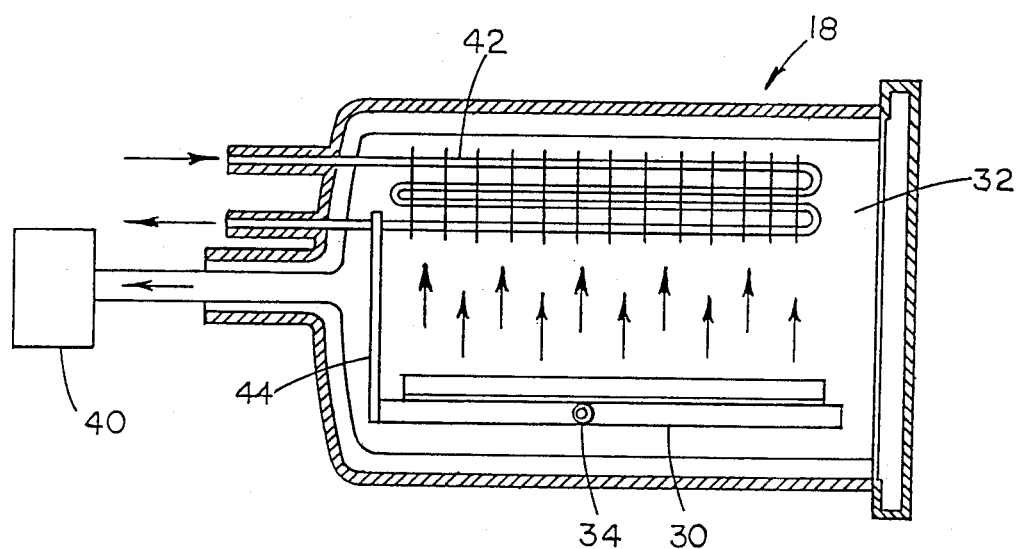
FIG. 7 is a diagrammatic vertical section view of a drying chamber of a freeze dryer utilizing the tray shown in FIG. 1.

The drying chamber 32 is adapted to be evacuated by a vacuum pump 40 (FIG. 7). A tube-type condensor 42 is superimposed above the shelves 30 and within the drying chamber 32. During the sublimation portion of the lyophilizing process, during which time the shelves 30 are heated and the drying chamber evacuated, the vapor driven from the wells 12 condenses as ice on the condensor. A baffle plate 45 prevents the vapors from being drawn directly out of the drying chamber 32 by the vacuum pump 40.

The dry heparin product pledget 20 is removed after lyophilization by simply turning the tray 10 upside down or by application of a relatively small air pressure supplied by a blower (not shown). The heparin pledget 20 has a predetermined U.S.P. unit value or dosage of heparin dependent upon both the initial concentration of the solution 16 and the volume of the wells 12 occupied by the solution.

It is imperative to successfully manufacturing the pledget 20 of heparin having a preset U.S.P. unit value that the solution 16 have a proper concentration corresponding to the volume of the wells 12. For a given well 12 having a set volume, the solution concentration must vary to obtain different unit values. Alternatively, for a set concentration of solution 14, the volume of the wells 12 must vary to vary the final unit dosage of the pledget 20.

It is first necessary, in the method of preparation of the solution 16, that a batch volume be determined. In describing the method or process or preparing the solution, a one thousand milliliter batch will be utilized to prepare pledgets 20 having one hundred units of heparin each. Variations in the procedure will be adaptable to alter unit dosages, either by varying the volume of the wells 12 or the concentration of solution 16.

If the solution 16 is to be one thousand milliliters, then the number of pledgets being made can be calculated by dividing the total volume of the batch, one thousand milliliters, by the volume of the wells, 73.3 microliters. This results in a finding that 13,642 pledgets can be made from a thousand milliliters initial batch.

The total units of heparin needed can then be calculated by multiplying the total number of pledgets times the units desired per pledget. A safety factor of ten units per pledget is added to insure that a minimum of one hundred units of heparin is obtained. This results in multiplication of 13,642 pledgets times one hundred ten units per pledget, equaling 1,500,620 units.

The weight in milligrams of a unit of heparin can be obtained from the label of the heparin container, the heparin being in a dry powder form. For example, a given lot may contain one hundred seventy-six U.S.P. units per milligram, which when divided into the total units, gives the weight of the heparin in grams, in this case 8,526 milligrams.

Figure 4:
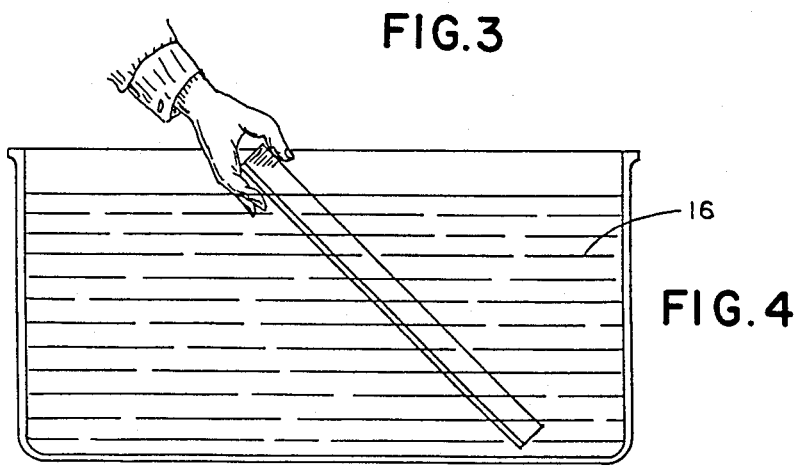
FIG. 4 is an elevational view showing a method for filling wells of the tray shown in FIG. 1 with a biological solution.

The dry heparin is weighed out and dissolved in the one thousand milliliters of sterile water and a one hundred unit solution 16 compatible with a well volume of 73.3 microliters results. The solution 16 is then transferred to the well 12, by an automatic pipette, not shown, or as shown in FIG. 4, by immersion of the tray 10 into the solution 16, which then fills the wells 12 in part by capillary action.

The lyophilization proceeds itself is the key to the success of creating a freeze dried pledget 20 of heparin. Four basic conditions are essential for freeze drying. First, the product must be solidly frozen below its eutectic point. Then, a condensing surface having a temperature less than minus forty degrees Centigrade is needed. The system must then be able to evacuate to an absolute pressure of between five and twenty-five microns of mercury (Hg). Finally, the system must have a heat source, controlled to temperatures between minus forty degrees Centigrade and plus sixty-five degrees Centigrade. The heat source supplies the heat of sublimation necessary to drive water vapor directly from the solid frozen ice.

During the freezing portion of the lyophilization process, the superimposed shelves 30 (FIGS. 3 and 6) receive refrigerated fluid through the conduits 34. The trays 10 are in turn supported on the freeze dryer shelves 30. Therefore, the conducting material 28 assists in rapidly and economically freezing the solution 16 below the solution eutectic point, which is necessary for complete freeze drying without danger of some moisture remaining in the matrix of the pledget 20. Remaining moisture can result in a condition known as "meltback", in which some water is returned to the pledget 20.

The cooler 36 is activated and the solution 16 is frozen in the wells 12. The proper freezing point is determined by matching the solution temperature to the shelf temperature and by visually observing that peaks are formed in the ice formed in the wells 12, the peaks indicating that the proper temperature gradient was maintained.

Once the freezing portion of the lyophilization process is complete, the frozen product is subjected to the heat of sublimation under evacuated conditions. This is the drying portion of the lyophilization process. The insulator 43 and plexiglass sheet 44 are removed to allow absolute pressure levels to be reached quickly and to avoid loss of air pockets in the insulator, if Styrofoam is used as the insulator 43.

The condensor 42 and vacuum pump 40 are activated at approximately the same time during the drying cycle. The condensor 42 is allowed to reach minus forty degrees Centigrade, while the vacuum in the drying chamber 32 should reach one hundred millitorr or less, at which pressure the thermally controlled shelves 30 are heated by activating the heater 38.

The frozen solution is dried for five to seven hours. The thermally controlled shelves 30 should, through the remainder of the lyophilization process drying cycle, be at about plus thirty degrees Centigrade, while the condenser 42 is in the range of minus forty-eight degrees Centigrade to minus sixty degrees Centigrade and the vacuum is maintained at between fifty and one hundred-fifty millitorr.

Once the drying cycle is completed, the vacuum is slowly released. Rapid release would cause the pledgets 20 to be blown out of the wells 12.

Figure 5:
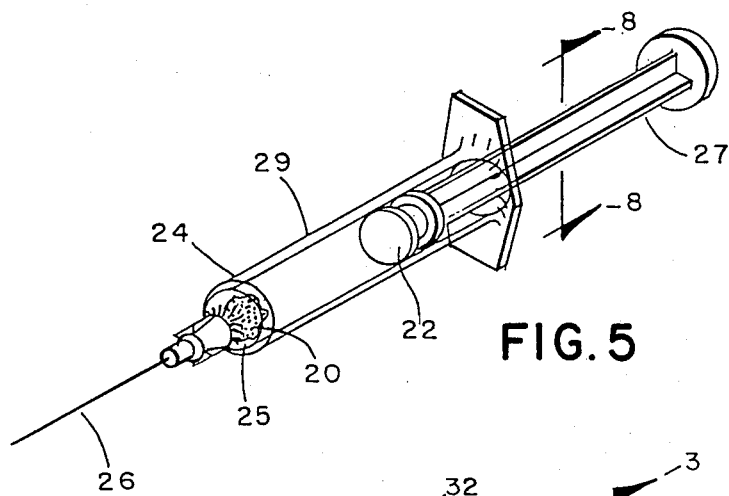
FIG. 5 is a perspective view of a syringe containing a dried pledget produced by the tray shown in FIG. 1.
Figure 8:
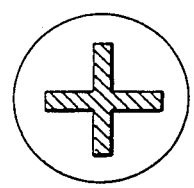
FIG. 8 is an enlarged sectional view taken in the plane of line 8—8 of FIG. 5.

Once lyophilized, the pledget 20 can be stored in a syringe 22 (FIG. 5). The pledget 20 is ready for immediate use in conjunction with the aspiration of a blood sample. The pledget 20 is placed inside a barrel 24 of the syringe 22, near an end member 25 of the barrel, to which end member is mounted an hypodermic needle 26. A plunger 27 of X-shaped cross section (FIG. 8) having a double-lipped sealing member 29 rotatably mounted at one end thereof is inserted along the barrel 24, placing the pledget 20 between the end member and sealing member.

The syringe 22, without a needle 26, but including the plunger 27 and sealing member 29, as well as the enclosed pledget 20, is placed in a sterile plastic envelope (not shown) and stored until such time as a patient's blood sample is needed. When the syringe is needed, the envelope is opened, the hypodermic needle 26 is attached, and the blood sample then aspirated from a blood-carrying vessel of the patient. It will be understood that once the pledget 20 contacts the blood, the pledget dissolves into solution, treating the blood at that time with anticoagulant properties and therefore allowing the blood to be analyzed for gas or other analysis, without interference from clotting.

While the present invention has been described with a certain degree of particularity, it is understood that the present disclosure has been made by way of example and that changes in the details of the structure and process may be made without departing from the spirit thereof.

What is claimed is:

1. A process involving lyophilization of biological material for producing pledgets of biological material in predetermined unit dosages for providing at least one of said pledgets in a syringe, comprising the steps of:
   providing a predetermined amount of liquid;
   providing a predetermined amount of biological material;
   providing a container including a top portion and having a plurality of wells formed in said container, each of said wells defining a volume for receiving a desired amount of biological material solution;
   forming a desired solution of biological material to produce pledgets of predetermined unit dosages using the magnitude of the predetermined amount of the liquid, the volume of each of said wells, and the predetermined magnitude of the amount of biological material;
   placing said biological material solution in said wells of said container;
   positioning said container in a chamber;
   lyophilizing said biological material solution in said wells using said chamber to produce pledgets, each of said pledgets having a predetermined dosage of biological material;
   removing each container from said lyophilizing chamber;
   exposing said pledgets of said biological material in said wells wherein said pledgets can be removed;
   removing each of said pledgets having a predetermined dosage of biological material from said plurality of wells, wherein said pledgets are separated from any apparatus used with said lyophilizing step; and placing at least one of said pledgets in a barrel of the syringe for use in preventing coagulation of blood.

2. A process, as claimed in claim 1, further including:

receiving blood into the syringe; and using at least said one pledget having a predetermined dosage of biological material to prevent coagulation of the blood received in the syringe barrel.

3. A process, as claimed in claim 1, wherein:

the step of providing a container includes providing a container having an upper layer in which said wells are formed and a lower layer made of a material having greater conductivity than said upper layer.

4. A process, as claimed in claim 1, wherein:

the step of placing said biological material solution into said wells includes immersing said container into a reservoir containing said biological material solution.

5. A process, as claimed in claim 1, wherein:

the step of placing said biological material solution into said wells includes directly contacting said wells with said biological material solution.

6. A process involving lyophilization for producing at least one pledget of biological material having a predetermined unit dosage, said one pledget being adapted to be placed in a syringe, comprising the steps of:

establishing a desired volume of water;

weighing out an amount of biological material;

providing a tray having a plurality of wells formed therein, each of said wells defining a volume;

forming a biological material solution to provide predetermined unit dosages of biological material using the magnitude of the volume of the water, the magnitude of the volume of each of said wells, and the magnitude of the amount of the biological material;

transferring said biological material solution to said tray by placing a portion of said biological material solution in each of said wells;

positioning said tray in a chamber;

lyophilizing said biological material in each of said wells to form pledgets having predetermined unit dosages of said biological material, said lyophilizing steps including:

insulating said tray to establish a temperature gradient that is cooler at the bottom of said biological material solution in said wells of said tray than at the top of said biological material solution in said wells of said tray, and stopping said insulating after said biological material solution has been frozen and prior to evacuating said chamber and heating said chamber;

removing said tray from said chamber after lyophilization;

exposing said pledgets having predetermined unit dosages of said biological material in said wells so that said pledgets can be removed; and removing said pledgets from each of said plurality of wells.

7. A process, as claimed in claim 6, further including the step of:

providing a cover on said tray during said insulating step to prevent contamination of said biological material.

* * * * *

UNITED STATES PATENT AND TRADEMARK OFFICE
CERTIFICATE OF CORRECTION

PATENT NO. : 4,521,975
DATED : June 11, 1985
INVENTOR(S) : Donald L. Bailey

It is certified that error appears in the above—identified patent and that said Letters Patent is hereby corrected as shown below:

column 7, line 45, delete "each" and substitute therefore --said--.

Signed and Sealed this

Seventeenth Day of September 1985

[SEAL]

Attest:

DONALD J. QUIGG

Attesting Officer

Commissioner of Patents and
Trademarks—Designate